United States Patent
Tarendeau

(10) Patent No.: US 9,944,974 B2
(45) Date of Patent: Apr. 17, 2018

(54) METHOD FOR THE SPECIFIC ISOLATION OF NUCLEIC ACIDS OF INTEREST

(71) Applicant: BIOMERIEUX, Marcy l'Etoile (FR)

(72) Inventor: Franck Tarendeau, Grenoble (FR)

(73) Assignee: BIOMERIEUX, Mancy l'Etoile (FR)

( * ) Notice: Subject to any disclaimer, the term of this patent is extended or adjusted under 35 U.S.C. 154(b) by 0 days.

(21) Appl. No.: 14/758,669

(22) PCT Filed: Jan. 27, 2014

(86) PCT No.: PCT/FR2014/050145
§ 371 (c)(1),
(2) Date: Jun. 30, 2015

(87) PCT Pub. No.: WO2014/114896
PCT Pub. Date: Jul. 31, 2014

(65) Prior Publication Data
US 2015/0337362 A1    Nov. 26, 2015

(30) Foreign Application Priority Data
Jan. 25, 2013 (FR) ..................................... 13 50650

(51) Int. Cl.
| C12Q 1/70 | (2006.01) |
| C12Q 1/68 | (2018.01) |
| C12Q 1/06 | (2006.01) |
| C12N 15/10 | (2006.01) |

(52) U.S. Cl.
CPC ....... C12Q 1/6806 (2013.01); C12N 15/1003 (2013.01); C12Q 1/06 (2013.01); C12Q 1/70 (2013.01)

(58) Field of Classification Search
None
See application file for complete search history.

(56) References Cited

U.S. PATENT DOCUMENTS

| 2010/0124763 A1 | 5/2010 | Walsh et al. |
| 2010/0129857 A1 | 5/2010 | Walsh et al. |

FOREIGN PATENT DOCUMENTS

| EP | 0745849 A2 | 12/1996 | | |
| WO | 2009/015484 A1 | 2/2009 | | |
| WO | WO 2009/015484 A1 * | 2/2009 | ............... | C12N 1/00 |
| WO | 2010/062350 A1 | 6/2010 | | |
| WO | WO 2010/062350 * | 6/2010 | ............... | C12M 1/34 |

OTHER PUBLICATIONS

"MolYsisTM Complete5", 2007 updated 2014.*
Mar. 17, 2014 Search Report issued in International Patent Application No. PCT/FR2014/050145.

* cited by examiner

Primary Examiner — Janet L Andres
Assistant Examiner — Stuart W Snyder
(74) Attorney, Agent, or Firm — Oliff PLC

(57) ABSTRACT

A method and diagnostic kit for selective isolation of microorganisms of interest and/or nucleic acids of interest including: a) bringing a liquid biological sample into contact with a saponin formulation to destabilize untargeted elements within the liquid biological sample, b) inducing osmotic shock of the untargeted elements to specifically lyse the untargeted elements, c) adding a solution of at least one enzyme capable of lysing free nucleic acids derived from the untargeted elements lysed in solution in the sample, and d) selectively obtaining the microorganisms of interest or the nucleic acids of interest. A precipitant of the unlyzed microorganisms of interest may be optionally added in solution. The microorganisms of interest have cell membranes or capsids that do not contain cholesterol. The untargeted elements may include untargeted cells having cell membranes containing cholesterol, and optionally viruses with envelopes containing cholesterol, mycoplasmas containing cholesterol, and cell debris.

19 Claims, No Drawings

METHOD FOR THE SPECIFIC ISOLATION OF NUCLEIC ACIDS OF INTEREST

The present invention relates to a method for selective isolation of microorganisms of interest and/or of nucleic acids of interest in a liquid biological sample containing or likely to contain, notably, numerous untargeted cells and/or numerous nucleic acids of untargeted cells. It also relates to the use thereof, diagnostic tests based on a method for isolating microorganisms of interest or on a method for isolating the nucleic acids of microorganisms of interest and kits for isolating microorganisms of interest and/or the nucleic acids of microorganisms of interest in a liquid biological sample comprising or likely to comprise, notably, microorganisms of interest, untargeted cells and, optionally, debris of microorganisms of interest and/or of untargeted cells.

The prior art consists of a certain number of scientific publications and patents. Thus, in 1992, Baker et al. described the use of a reagent called saponin for lysing human cells differentially and isolating the plasmodium pathogen from whole blood. They demonstrated that saponin with a low final concentration, of the order of 0.015%, can lyse human cells in 20 µL of citrate-buffered whole blood and supply enough clean lysate for performing PCR detection.

Patent application EP-A-0,745,849 revisited this differential approach of using saponin for larger volumes of whole blood (5 mL) with a final concentrated saponin solution of the order of 0.020-0.125%.

Another patent application EP-A-2,185,681 proposes a method of preparing the saponin solutions, using a more concentrated saponin solution, i.e. with a final concentration between 2 and 10% for a volume of whole blood of average size, i.e. 5 mL. This invention proposes using hypotonic or physiological buffers for saponin solutions of this kind.

However, at present, no rapid solution is available for isolating and identifying a very small amount of pathogenic cells within voluminous biological samples. For example, for septicaemia, it is necessary to be able to identify from 1 to 10 colony-forming units (CFU) of pathogens in 10 mL of whole blood within less than 6 hours, or in the most difficult cases 1 fg of nucleic acid of targeted pathogen in more than 800 µg of untargeted (human) nucleic acids.

The problems encountered in diagnostics of infectious diseases are therefore:
1) complexity of the matrix sample ordinarily including very few cells of pathogens, on the one hand, and a very large number of human cells, and other cells or particles, on the other hand, which must be removed so that they do not interfere with isolation and identification of the pathogens, and
2) the physical limitations to isolation of a very small number of pathogens from a very large sample volume.

To summarize, the challenge is to remove the maximum amount of untargeted elements (cells and/or particles) while retaining the maximum amount of pathogenic targets, few of which were present initially, in order to increase their concentration artificially and facilitate their detection.

The invention described here is a method that can isolate and identify a small number of pathogens from large volumes of biological samples (for example of the order of 10 ml) in a relatively short time. These pathogens are, non-exhaustively, bacteria, viruses and fungi. The invention makes it possible to identify quantities as small as 3 CFU in 10 mL of whole blood (i.e. 0.3 CFU/mL), with a limit of detection never previously described in the literature. Its novelty is based on:

1. An attractive limit of detection never attained previously, of the order of 0.3 CFU/mL, relative to the clinical requirement, which is from 0.1 to 1 CFU/mL.
2. The ability to use various whole bloods buffered with EDTA or with citrate, but also with heparin. Heparin is a reagent that is much used in hospitals, but is often rejected in molecular biology approaches owing to its capacity for preventing amplification of nucleic acids and reactions based on enzyme(s). This invention can manage blood buffered with heparin, which is not generally the case with the molecular methods described in the literature.
3. Capacity for using large volumes of whole blood of 10 mL or more.
4. The use of polyethylene glycol (PEG) for improving precipitation of the pathogens. The precipitation of DNA or of viruses by PEG is described very well in the literature. However, the use of PEG for precipitating bacterial cells or fungi such as yeasts is absent from the state of the art. Since saponin is a reagent similar to detergents, the pathogenic cells or particles may float inside the tube or experience difficulties in precipitating to the bottom of a tube under the effect of centrifugation. Even if it is not required for certain treated samples, addition of PEG guarantees precipitation of the targets that is constant without the risk of floating. Moreover, this addition of PEG improves the adhesion of pellets containing pathogens on the plastic tube and the resistance to surface washings.
5. Combining differential lysis with saponin with treatments based on highly concentrated nucleases; in other words, lysis of non-target cells, which will release their nucleic acids, which on a second occasion will be degraded by treatment with nucleases. This differential lysis releases a large amount of human nucleic acids. Typically 880 µg of human DNA can be extracted from 10 ml of whole blood. These human nucleic acids are the source of considerable problems when the aim is to detect a very low copy number of pathogenic nucleic acids:
   i) they compete during purification of the pathogenic target nucleic acids, saturating the nucleic acid capture reagents owing to their excess (for example silica membranes, magnetic silica beads, chromatography or affinity matrices, etc.),
   ii) they interfere during amplifications of the pathogenic molecules. With maximum removal of human nucleic acids, the limits of detection are improved. According to these critical points, the invention uses a large amount of nucleases to remove a maximum of human nucleic acids after lysis with saponin. Combining saponin with a treatment with highly concentrated nucleases has never been described in the literature.
6. Finally, we have demonstrated that buffered saponin solution, with a pH between 6 and 9, can prevent precipitation of undesirable elements of the blood, particularly red blood cells. Previously, scientists have used buffers close to pH 7 for the saponin solution, but without ever correlating the effect of this pH with the stability of the sample.

To summarize, the present invention combines different uses of chemicals for attaining a limit of detection of pathogen compatible with the values of detection of a clinical range (0.1 to 1 CFU/mL). The combined use of saponin with PEG and at least one nuclease has never been described and allows a technical improvement that was unknown hitherto. Combining of these reagents may be complete (saponin+PEG+nuclease) or partial (saponin+ nuclease or saponin+PEG only or else PEG only) for preparing the sample for analysis for identification or for detection.

For this purpose, the present invention relates to a method for selective isolation of microorganisms of interest in a liquid biological sample comprising or likely to comprise, notably:
microorganisms of interest whose cell membrane or capsid does not contain cholesterol, and
untargeted elements, i.e.:
untargeted cells whose cell membrane contains cholesterol, and
optionally, viruses with envelopes containing cholesterol, and
optionally mycoplasmas containing cholesterol, and
optionally, debris of microorganisms of interest and/or of untargeted cells,
said method comprising the following steps:
a) bringing the liquid biological sample into contact with a saponin formulation, in order to destabilize the cell membranes containing cholesterol or the viral envelopes containing cholesterol or the mycoplasma membranes containing cholesterol,
b) carrying out osmotic shock of the untargeted cells in order to lyse them specifically,
c) adding a solution of at least one enzyme able to lyse the free nucleic acids (DNA and/or RNA) derived from the untargeted elements lysed in solution in the sample, allowing the microorganisms of interest to be obtained selectively.

The present invention also covers a method for selective isolation of microorganisms of interest in a liquid biological sample comprising or likely to comprise, notably:
microorganisms of interest whose cell membrane or capsid does not contain cholesterol, and
untargeted elements, i.e.:
untargeted cells whose cell membrane contains cholesterol, and
optionally, viruses with envelopes containing cholesterol, and
optionally mycoplasmas containing cholesterol, and
optionally, debris of microorganisms of interest and/or of untargeted cells,
said method comprising the following steps:
a) bringing the liquid biological sample into contact with a saponin formulation, in order to destabilize the cell membranes containing cholesterol and/or the viral envelopes containing cholesterol and/or the membranes of the mycoplasmas containing cholesterol,
b) performing osmotic shock of the untargeted cells in order to lyse them specifically,
c) adding an agent for precipitating the unlysed microorganisms of interest in solution in the sample, allowing the microorganisms of interest to be obtained selectively.

According to a third embodiment, the invention covers a method for selective isolation of microorganisms of interest in a liquid biological sample comprising or likely to comprise, notably:
microorganisms of interest whose cell membrane or capsid does not contain cholesterol, and
untargeted elements, i.e.:
untargeted cells whose cell membrane contains cholesterol, and
optionally, viruses with envelopes containing cholesterol, and
optionally mycoplasmas containing cholesterol, and
optionally, debris of microorganisms of interest and/or of untargeted cells,
said method comprising the following steps:
a) bringing the liquid biological sample into contact with a saponin formulation, in order to destabilize the cell membranes containing cholesterol and/or the viral envelopes containing cholesterol and/or the membranes of mycoplasmas containing cholesterol,
b) performing osmotic shock of the untargeted cells in order to lyse them specifically,
c) adding an agent for precipitating the unlysed microorganisms of interest in solution in the sample, and
d) adding a solution of at least one enzyme able to lyse the free nucleic acids (DNA and/or RNA) derived from the untargeted elements lysed in solution in the sample, allowing the microorganisms of interest to be obtained selectively.

Step c) of this last-mentioned method may be carried out independently of step a), after steps a) and b) or after step d).

The present invention also relates to a method for selective isolation of nucleic acids of interest in a liquid biological sample comprising or likely to comprise, notably:
microorganisms of interest whose cell membrane or capsid does not contain cholesterol, and
untargeted elements, i.e.:
untargeted cells whose cell membrane contains cholesterol, and
optionally, viruses with envelopes containing cholesterol, and
optionally mycoplasmas containing cholesterol, and
optionally, debris of microorganisms of interest and/or of untargeted cells,
said method comprising the following steps:
a) bringing the liquid biological sample into contact with a saponin formulation, in order to destabilize the cell membranes containing cholesterol and/or viral envelopes containing cholesterol and/or the membranes of mycoplasmas,
b) performing osmotic shock of the untargeted cells in order to lyse them specifically,
c) adding a solution of at least one enzyme able to lyse the free nucleic acids (DNA and/or RNA) derived from the untargeted elements lysed in solution in the sample,
d) inactivating the enzyme added in step (c), and
e) making accessible the nucleic acids of microorganisms of interest not degraded by the enzyme of step (c).

According to a fifth embodiment, the invention covers a method for selective isolation of nucleic acids of interest in a liquid biological sample comprising or likely to comprise, notably:
microorganisms of interest whose cell membrane or capsid does not contain cholesterol, and
untargeted elements, i.e.:
untargeted cells whose cell membrane contains cholesterol, and
optionally, viruses with envelopes containing cholesterol, and
optionally mycoplasmas containing cholesterol, and
optionally, debris of microorganisms of interest and/or of untargeted cells, said method comprising the following steps:
  a) bringing the liquid biological sample into contact with a saponin formulation, in order to destabilize the cell membranes containing cholesterol and/or the viral envelopes containing cholesterol and/or the membranes of mycoplasmas containing cholesterol,
  b) performing osmotic shock of the untargeted cells in order to lyse them specifically,
  c) adding an agent for precipitating the unlysed microorganisms of interest in solution in the sample, and
  d) making accessible the nucleic acids of microorganisms of interest not accessible by the action of steps a) and b).

According to a sixth embodiment, the invention covers a method for selective isolation of nucleic acids of interest in a liquid biological sample comprising or likely to comprise, notably:
  microorganisms of interest whose cell membrane or capsid does not contain cholesterol, and
  untargeted elements, i.e.:
    untargeted cells whose cell membrane contains cholesterol, and
    optionally, viruses with envelopes containing cholesterol, and
    optionally mycoplasmas containing cholesterol, and
    optionally, debris of microorganisms of interest and/or of untargeted cells,
said method comprising the following steps:
  a) bringing the liquid biological sample into contact with a saponin formulation, in order to destabilize the cell membranes containing cholesterol and/or the viral envelopes containing cholesterol and/or the membranes of mycoplasmas containing cholesterol,
  b) performing osmotic shock of the untargeted cells in order to lyse them specifically,
  c) adding an agent for precipitating the unlysed microorganisms of interest in solution in the sample, and
  d) adding a solution of at least one enzyme able to lyse the free nucleic acids (DNA and/or RNA) derived from the untargeted elements lysed in solution in the sample,
  e) inactivating the enzyme added in step (d),
  f) obtaining the nucleic acids of microorganisms of interest:
    not degraded by the enzyme of step (d), and
    not accessible by the action of steps a) and b).

Step c) of this last-mentioned method may be carried out independently of step a), after steps a) and b) or after step d).

According to a seventh aspect, the present invention also relates to an improved method of precipitation of the microorganisms of interest selected from bacteria and fungi (preferably yeasts), consisting of adding at least one precipitant, in liquid biological samples, if necessary treated beforehand with saponin.

Addition of precipitant(s) makes it possible to improve the efficiency of precipitation of the microorganisms contained in a liquid biological sample.

Whatever the embodiment, the method of isolation is characterized in that the saponin is in a volume at least greater than or equal to the volume of the sample at the same concentration.

The final saponin concentration is above 0.02% and less than or equal to 20%, preferably between 0.05% and 20%, more preferably between 0.5 and 20% and even more preferably between 0.08 and 4%.

Osmotic shock of the untargeted cells in order to lyse the latter specifically is a property inherent in bringing the liquid biological sample into contact with the saponin formulation as described in step a). This saponin formulation is used in large volume, which has the effect of:
  weakening or destabilizing the cell membranes containing cholesterol, namely the membranes of the untargeted cells, and at the same time
  inducing an osmotic pressure, which will lead to turgescence of the untargeted cells and lysis thereof.

In other words, steps a) and b) may be rewritten as a single step consisting of bringing the liquid biological sample into contact with a saponin formulation in order to lyse specifically the cell membranes of the untargeted cells containing cholesterol and the viral envelopes containing cholesterol and the membranes of the mycoplasmas containing cholesterol.

The method of isolation is also characterized in that the saponin consists of a triterpenoid.

Saponin is specific to membranes or envelopes containing cholesterol.

In the context of the method for isolating microorganisms of interest and of the improved method of precipitation of microorganisms of interest according to the invention, the precipitant used is selected from PEG, glycogen and the nucleic acids (DNA/tRNA etc.). It is also possible to use a mixture thereof.

The precipitant preferably used is PEG.

In the context of the method for isolating nucleic acids of microorganisms of interest, the precipitant may consist of polyethylene glycol (PEG).

The concentrations of precipitant used in the context of the invention are between 0.1% and 20%, preferably between 1% and 20%.

At the end of the method for isolating the microorganisms of interest, whatever the embodiment thereof, it is possible to treat the medium obtained for further isolation of the microorganisms of interest, thus allowing detection thereof. This is done using conventional cellular techniques, for example cytology techniques (flow cytometry or others), immunology techniques (technology with antibodies or phages for detection by immunoassay) or classical cell culture techniques.

Thus, it is possible to apply the medium obtained for conventional culture on a suitable medium, preferably on a solid medium (for example a nutrient agar medium) in a Petri dish for at least 24 h, for example 48h for yeasts, at a suitable temperature, for example 30° C. for yeasts, preferably 37° C., or any medium suitable for growth of the microorganisms of interest. Any known technique and protocol allowing growth of the microorganisms and then individualization/isolation thereof may also be used.

According to certain variants of carrying out the method of isolation, the enzyme able to lyse the free nucleic acids is an enzyme which is then inactivated:
  chemically by adding EDTA and/or EGTA and/or DTT and/or β-mercaptoethanol and/or DEPC, and/or guanidine, and/or
  physically by increasing the temperature between 40 and 100° C. in the presence or in the absence of detergents, such as sodium dodecyl sulphate (SDS).
  in cases when the method of isolation according to the invention only comprises a single enzyme able to lyse the free nucleic acids (DNA and/or RNA) derived from the untargeted elements lysed in solution in the sample, this enzyme is a DNase.

According to certain variants of carrying out the method of isolation where at least one enzyme is added that is able to lyse the free nucleic acids, i.e. during step (c) when the method used does not comprise a step of adding precipitant or during step (d) when the method comprises a step of adding precipitant, the enzyme able to lyse the free nucleic acids is an enzyme that may be inactivated:

chemically by adding EDTA and/or EGTA and/or DTT and/or β-mercaptoethanol and/or DEPC, and/or guanidine, and/or physically by increasing the temperature between 40 and 100° C. in the presence or in the absence of detergents, such as sodium dodecyl sulphate (SDS).

In the methods for isolating microorganisms of interest and for isolating nucleic acids of microorganisms of interest according to the invention comprising a step of adding precipitant and a step of adding at least one enzyme able to lyse the free nucleic acids (DNA and/or RNA) derived from the untargeted elements lysed in solution in the sample, these two steps do not have a defined order and may be reversed in the execution of the method.

In the context of the method for isolating nucleic acids of microorganisms of interest according to the invention comprising a step of inactivating the enzyme able to lyse the free nucleic acids, the precipitant may be added after this inactivation step.

The invention also relates to a method for isolating microorganisms of interest or for isolating nucleic acids of microorganisms of interest or for precipitating microorganisms of interest, in a liquid biological sample, preferably of blood, characterized in that during the method, the pH is maintained in a range between 5 and 10, preferably between 6 and 9, by adding a solution that is:

basic if the pH is below 5, preferably below 6, acidic if the pH is above 10, preferably above 9, so that the pH is within the range.

According to a variant of use, the invention uses a saponin formulation leading to a final concentration above 0.02% and less than or equal to 20%, preferably above 0.05% and less than or equal to 20% and/or a precipitating agent (or precipitant) at a concentration from 0.1 to 20%, preferably 0.1 to 4%, even more preferably from 0.5 to 4%, and/or an enzyme able to lyse the free nucleic acids (DNA and/or RNA) containing between 500 and 20000 enzyme units.

According to another of its aspects, the invention covers the use of a saponin formulation and of a solution of at least one enzyme able to lyse the free nucleic acids (DNA and/or RNA) and optionally at least one precipitant, preferably selected from PEG, glycogen and the nucleic acids (preferably DNA, tRNA), for isolation of microorganisms of interest or of nucleic acids of microorganisms of interest, in a liquid biological sample.

According to another of its aspects, the present invention covers the use of PEG for precipitation of microorganisms of interest, preferably of bacteria and fungi (preferably yeasts), in liquid biological samples, if necessary treated beforehand with saponin.

The invention further relates to a diagnostic test based on a method for isolating microorganisms of interest, as described above, or on the uses for isolation of the microorganisms of interest, as described above, or on a method of precipitation of microorganisms as described above.

The invention also relates to a diagnostic test based on a method for isolating nucleic acids of microorganisms of interest, as described above, or on the uses for isolation of the nucleic acids of microorganisms of interest, as described above.

The diagnostics may be carried out by conventional techniques known by a person skilled in the art, employing, for example, classical techniques of detection used in microbiology, immunoassay techniques or classical molecular biology techniques such as PCR, NASBA etc.

The invention also relates to a diagnostic kit for isolating microorganisms of interest in a liquid biological sample comprising or likely to comprise, notably, microorganisms of interest, untargeted cells and, optionally, viruses with envelopes, mycoplasmas and/or debris of microorganisms of interest and/or of untargeted cells, said kit comprising:

(a) a container, and (b) at least one saponin formulation, and (c) at least one solution of a precipitant, such as polyethylene glycol (PEG).

The invention finally relates to a diagnostic kit for isolating the nucleic acids of microorganisms of interest in a liquid biological sample comprising or likely to comprise, notably, microorganisms of interest, untargeted cells and, optionally, enveloped viruses, mycoplasmas and/or debris of microorganisms of interest and/or of untargeted cells, said kit comprising:

(a) a container, and (b) at least one saponin formulation, and (c) at least one solution of a precipitant, such as polyethylene glycol (PEG).

The two kits described above may further comprise (d) at least one solution of at least one enzyme able to lyse the nucleic acids.

The kit further comprises:

(c) or (d') at least one acid solution and/or at least one basic solution, and/or (d) EDTA and/or EGTA and/or DTT and/or β-mercaptoethanol and/or DEPC, and/or guanidine and/or (e) at least one detergent or an anionic agent.

In the present description, the enzyme or enzymes allowing lysis of the nucleic acids are enzymes that are known and are used conventionally by a person skilled in the art, such as DNAse I, RNAseIf etc., and the step consisting of making accessible the nucleic acids of the microorganisms of interest is carried out in a conventional manner that is known by a person skilled in the art, for example by mechanical lysis and then purification of the nucleic acids and PCR amplification or any other known technique.

In the rest of this patent application, the terms used have the following definitions:

"Viral envelope" means the envelope of enveloped viruses, which contains cholesterol, in contrast to the capsid of capsid viruses, which does not contain cholesterol. The viral envelope is therefore sensitive to saponin.

"Destabilize the cell membranes and/or viral envelopes and/or the membranes of mycoplasmas" means the physicochemical mechanisms leading to a loss of regulation of osmolarity at the membrane level and/or the level of the viral envelope and/or of the membrane of a mycoplasma, disturbance of membrane transport and the potential appearance of pores at the level of the cell membrane, mycoplasma membrane or viral envelope.

The term "microorganisms of interest" comprises all microorganisms that do not contain accessible cholesterol, which are potentially pathogenic, notably for humans. These microorganisms include viruses (with the exception of the enveloped viruses), bacteria, fungi (yeasts), but also microscopic animals.

"Nucleic acids of interest" correspond to the nucleic acids (DNA and RNA) contained in the cells or particles of the "microorganisms of interest" defined above.

"Untargeted cells" are to be understood as all cells of living organisms that do not contain "nucleic acids of interest" as defined above.

The abbreviation "EDTA" corresponds to ethylenediaminetetraacetic acid.

The abbreviation "EGTA" corresponds to ethylene glycol tetraacetic acid.

The abbreviation "DTT" corresponds to dithiothreitol.

The abbreviation "DEPC" corresponds to diethylpyrocarbonate.

CFU stands for colony-forming unit.

The term "detergents" means all classes of molecules that may induce a physicochemical modification of other molecules. These detergents may be of a chemical nature such as SDS, Tween-20, Triton X-100, brij97, or may be enzymatic.

"Liquid biological sample" is to be understood as a liquid sample that may contain the "microorganisms of interest" selected from the following group: amniotic fluid, aqueous humour, bile, blood, mammary secretion, bronchoalveolar wash, cerebrospinal fluid, chyle, chyme, faeces, interstitial fluid, lymph, menstrual fluid, mucus, plasma, pleural fluid, pus, saliva, sebum, sperm, serum, sputum, sweat, synovial fluid, tears, urine and vitreous humour.

Moreover, it has to be clear that the method for selective isolation of nucleic acids of interest as described above and the use thereof allow isolation of the microorganisms of interest, to the extent that the nucleic acids of interest correspond to the nucleic acids (DNA and/or RNA) contained in the cells or particles of the microorganisms of interest. In other words, selective isolation of the nucleic acids of interest allows isolation of the microorganisms of interest from which the nucleic acids of interest are derived.

The accompanying examples are presented for demonstrating the efficacy of the method according to the invention and are given for purposes of illustration and are not exhaustive.

EXAMPLE 1: DETECTION OF 5 AND 10 CFU OF *PSEUDOMONAS AERUGINOSA* IN 10 ML OF WHOLE BLOOD TREATED WITH 4% SAPONIN SOLUTION

In a 50-mL plastic tube, 20 mL of whole blood treated with EDTA was inoculated with 20, 10, 2 and 0 (negative control) CFU of *Pseudomonas aeruginosa*. The number of CFU inserted in the blood was verified by streaking on agar media in a Petri dish. The 20 mL of inoculated blood was divided into two and each 10-mL volume was deposited in two 50-mL plastic tubes to provide duplicates. Forty milliliters of filtered 4% saponin solution, 50 mM Tris-HCl at pH 8.0 and 4% of PEG-8000 were added to the inoculated blood. The tubes were agitated by inverting twice, incubated at room temperature for 5 minutes and centrifuged at 12000 g for 10 minutes. The supernatant was removed and the adhering pellet was washed three times with 15 mL of 4% PEG-8000, which prevents detachment of the pellet. A volume of 200 µL of 10 mM Tris-HCl at a pH of 7.5 was added to the pellet.

Next, 10 µL of DNAse I (500 u/pµl; Roche) and 2 µL RNAse If (50 u/µL; New England Biolabs) were put in the tubes. The pellets were digested with the enzymes for 10 minutes, agitating twice by vortexing after 2 minutes and 4 minutes of incubation. After digestion with the nucleases, 10 µL of EDTA at 0.5 M and pH 8.0 was added to the tubes. The samples were transferred to microtubes with a capacity of 1.5 mL, containing 200 mg of glass beads with a diameter of 1 mm and 50 mg of zirconium beads with a diameter of 0.1 mm. The microtubes were heated for 10 minutes at 80° C. Then 20 µL of proteinase K (Novagen) and 40 µL of 10% SDS were added to the tubes. The microtubes were incubated for 5 minutes at room temperature and heated for 5 minutes at 80° C.

Mechanical lysis of the *Pseudomonas* cells was performed by agitating the tubes containing the beads for 20 minutes using a vortex. The DNA present in the lysis supernatant was purified using the Nucleospin Blood® kit from Macherey-Nagel. Quantitative PCR amplification was performed using the full eluate, or 40 µl. The samples with 5 CFU of *Pseudomonas aeruginosa* were detected well on a replica by means of the invention, and partial detection of one replica out of two was observed for 1 CFU inserted, as is quite clear from Table I below:

TABLE I

Evaluation of the limit of detection for *Pseudomonas aeruginosa* using the method according to the invention

| Sample | Cq | Number of replicas detected |
|---|---|---|
| 10 CFU total | 38.78 | 2/2 |
| 10 CFU total | 37.74 | |
| 5 CFU total | 42.18 | 2/2 |
| 5 CFU total | 37.84 | |
| 1 CFU total | 41.73 | 1/2 |
| 1 CFU total | N/A* | |
| Negative control | N/A* | 0/2 |
| Negative control | N/A* | |

*no fluorescence signal was detected after 50 amplification cycles.

EXAMPLE 2: DETECTION OF 28 AND 140 CFU OF *CANDIDA ALBICANS* IN 10 ML OF WHOLE BLOOD TREATED WITH 4% SAPONIN SOLUTION

In a 50-mL plastic tube, 20 mL of whole blood treated with EDTA was inoculated with 140, 28 and 0 (negative control) CFU of *Candida albicans*. The number of CFU inserted in the blood was verified by streaking on agar media in a Petri dish. The 20 mL of blood inoculated was divided into two and each 10-mL volume was deposited in two 50-mL plastic tubes to provide duplicates. Forty milliliters of filtered 4% saponin solution, 50 mM Tris-HCl at pH 8.0 and 4% of PEG-8000 were added to the inoculated blood. The tubes were agitated by inverting twice, incubated at room temperature for 5 minutes and centrifuged at 12000 g for 10 minutes. The supernatant was removed and the pellet was washed three times with 15 mL of 4% PEG-8000, which prevents detachment of the pellet. A volume of 200 µL of 10 mM Tris-HCl at a pH of 7.5 was added to the pellet. Next, 10 µL of DNAse I (500µ/µL; Roche) and 2 µL RNAse If (50µ/µL; New England Biolabs) were put in the tubes. The pellets were digested with the enzymes for 10 minutes, agitating twice by vortexing after 2 minutes and 4 minutes of incubation. After digestion with the nucleases, 10 µL of EDTA at 0.5 M and pH 8.0, a volume of 40 µl of 10% SDS and 20 µl of proteinase K were added to the tubes. The samples were transferred to microtubes with a capacity of 1.5 mL, containing 200 mg of glass beads with a diameter of 1 mm and 50 mg of zirconium beads with a diameter of 0.1 mm. The microtubes were heated for 60 minutes at 80°

C. Mechanical lysis of the *Candida albicans* cells was performed by agitating the beads for 20 minutes using a vortex. The DNA present in the lysis supernatant was purified using the Nucleospin Blood® kit from Macherey-Nagel and purified a second time using the gDNA Clean-up XS® kit from Macherey-Nagel. Quantitative PCR amplification was performed using the full eluate, i.e. 40 µL. The samples with 28 CFU of *Candida albicans* were detected on a replica by means of the invention, as is clearly shown in Table 2 below:

TABLE 2

Detection of *Candida albicans* using the method according to the invention

| Sample | Cq | Number of replicas detected |
| --- | --- | --- |
| 140 CFU total | 37.44 | 2/2 |
| 140 CFU total | 36.78 | |
| 28 CFU total | 40.08 | 2/2 |
| 28 CFU total | 38.42 | |
| Negative control | N/A* | 0/1 |

*no fluorescence signal was detected after 50 amplification cycles.

EXAMPLE 3: DETECTION OF 20000 VIRIONS OF HUMAN ADENOVIRUS 5 IN 10 ML OF WHOLE BLOOD TREATED WITH 4% SAPONIN SOLUTION

In a 50-mL plastic tube, 10 mL of whole blood treated with EDTA was inoculated with 20000 virions of human Adenovirus 5. Forty milliliters of filtered 4% saponin solution, with 50 mM Tris-HCl at pH 8.0 and 4% of PEG-8000 were added to the inoculated blood. The tubes were agitated by inverting twice, incubated at room temperature for 5 minutes and centrifuged at 12000 g for 10 minutes. The supernatant was removed and the pellet was washed three times with 15 mL of 4% PEG-8000, which prevents detachment of the pellet. A volume of 200 µL of Tris-HCl at 10 mM and at a pH of 7.5 was added to the pellet. Next, 10 µL of DNAse I (500µ/µl; Roche) and 2 µL RNAse If (50µ/µL; New England Biolabs) were put in the tubes. The pellets were digested with the enzymes for 10 minutes, agitating twice by vortexing after minutes and 4 minutes of incubation. After digestion with the nucleases, 10 µL of 0.5 M EDTA, pH 8.0 and 40 µl of 10% SDS were added to the tubes. The samples were transferred to microtubes with a capacity of 1.5 mL, containing 200 mg of glass beads with a diameter of 1 mm and 50 mg of zirconium beads with a diameter of 0.1 mm. The microtubes were heated for 10 minutes at 80° C. Mechanical lysis of the virions was performed by agitating the tubes containing the beads for 20 minutes using a vortex. The DNA present in the lysis supernatant was purified using the Nucleospin Bloody kit from Macherey-Nagel. The nucleic acids were eluted with 40 µl. Quantitative PCR amplification was performed using 10 µl of eluate. The 20000 virions were detected well by means of the invention, see Table 3 below:

TABLE 3

Evaluation of the limit of detection of human Adenovirus 5 by means of the invention

| Sample | Cq | Number of replicas detected |
| --- | --- | --- |
| 20000 virions total | 34.7 | 1/1 |

EXAMPLE 4: EFFICACY OF LYSIS OF HUMAN BLOOD CELLS WITH VARIOUS CONCENTRATIONS OF SAPONIN

In a 50-mL plastic tube, 10 mL of whole blood treated with EDTA was inoculated with 24 and 0 (negative control) CFU of *Pseudomonas aeruginosa*. The number of CFU inserted in the blood was verified by streaking on agar media in a Petri dish. Forty milliliters of filtered saponin solution, 50 mM Tris-HCl at pH 8.0 and 4% of PEG-8000 were added to the inoculated blood. The final saponin concentrations were 0.005%, 0.02%, 0.08% and 0.4%. Each concentration was tested in duplicate. The tubes were agitated by inverting three times, incubated at room temperature for 10 minutes and centrifuged at 12000 g for 10 minutes. The supernatant was removed and the adhering pellet was washed three times with 15 mL of 4% PEG-8000, which prevents detachment of the pellet. A volume of 400 µL of 10 mM Tris-HCl at a pH of 7.5, 2.5 mM $MgCl_2$, 0.5 mM $CaCl_2$, DNAse I (Roche) 5000 u, RNAse If (New England Biolabs) 100 u was added to the pellet. The pellets were incubated at 32° C. with stirring for 90 minutes. The samples were transferred to microtubes containing 10 µL of 0.5 M EDTA at pH 8.0 and 400 µl of buffer B3 (Macherey-Nagel). The microtubes were heated for 10 minutes at 80° C. and then cooled for 5 min in ice. 5 µg of lysine was added to the tubes. The microtubes were incubated for an additional 10 minutes in ice and then were treated using the Nucleospin Blood® kit from Macherey-Nagel according to the supplier's conditions but doubling the amounts of proteinase K and of ethanol, in keeping with the ratios of the reagents. Quantitative PCR amplification was performed using 2 µl of eluate for detecting human DNA and 38 µL for the PCRs for detecting the DNA of *Pseudomonas aeruginosa*. Most of the tubes were positive for *Pseudomonas aeruginosa* (the negative controls, uninoculated bloods, treated with 0.4% of saponin being definitely negative). The example shows that it is possible to detect *Pseudomonas aeruginosa* for saponin concentrations well below 0.4%.

The amplifications for the final saponin concentrations greater than or equal to 0.08% did not succeed in detecting human DNA or extremely small quantities (Table 4). In contrast, for the final saponin concentrations less than or equal to 0.02%, the amounts of human DNA detected are very high (Cq around 28). This demonstrates that at a final saponin concentration less than or equal to a value of 0.02%, the white blood cells are no longer correctly lysed whereas they are lysed very well with a final saponin concentration of 0.08% or 0.4%.

TABLE 4

Evaluation of the lysis of human blood cells

| Sample | Cq (human DNA) | Number of tubes positive for P. Aeruginosa |
|---|---|---|
| Negative control 0.4% saponin | Not detected* | 0/2 (Controls) |
| Negative control 0.4% saponin | Not detected* | |
| 0.4% saponin | 39.16 | 2/2 |
| 0.4% saponin | Not detected* | |
| 0.08% saponin | Not detected* | 1/2 |
| 0.08% saponin | Not detected* | |
| 0.02% saponin | 27.35 | 2/2 |
| 0.02% saponin | 27.99 | |
| 0.005% saponin | 28.63 | 1/2 |
| 0.005% saponin | 29.27 | |

*no fluorescence signal was detected after 50 amplification cycles.

EXAMPLE 5: DETECTION OF 21 CFU OF PSEUDOMONAS AERUGINOSA IN 10 ML OF WHOLE BLOOD TREATED WITH 0.4% SAPONIN SOLUTION

In a 50-mL plastic tube, 10 mL of whole blood treated with EDTA was inoculated with 21 (5 tubes) and 0 (negative control, 1 tube) CFU of Pseudomonas aeruginosa. The number of CFU inserted in the blood was verified by streaking on agar media in a Petri dish. Forty milliliters of filtered 0.4% saponin solution, 50 mM Tris-HCl at pH 8.0 and 4% of PEG-8000 were added to the inoculated blood. The tubes were agitated by inverting three times, incubated at room temperature for 10 minutes and centrifuged at 12000 g for 10 minutes. The supernatant was removed and the adhering pellet was washed three times with 15 mL of 4% PEG-8000, which prevents detachment of the pellet. A volume of 800 µL of 10 mM Tris-HCl at a pH of 7.5, 2.5 mM $MgCl_2$, 0.5 mM $CaCl_2$, DNAse I (Roche) 5000 u, RNAse If (New England Biolabs) 100 u was added to the pellet. The pellets were incubated at 32° C. with stirring for 90 minutes. 10 µL of 0.5 M EDTA at pH 8.0 and 400 µl of buffer B3 (Macherey-Nagel) were added and then the tubes were heated for 10 minutes at 80° C. and were then cooled for 5 min in ice. 5 µg of lysine was added to the tubes. The tubes were incubated for an additional 10 minutes in ice and then were treated using the Nucleospin Blood® kit from Macherey-Nagel according to the supplier's conditions but quadrupling the amounts of proteinase K and of ethanol, in keeping with the ratios of the reagents. Quantitative PCR amplification was performed using 2 µl of eluate for detecting human DNA and 38 µL for the PCRs for detecting the DNA of Pseudomonas aeruginosa.

TABLE 5

Quantitative PCR for detecting the DNA of P. aeruginosa

| Sample | Cq (P. aeru. DNA) | Number of tubes positive for P. Aeruginosa |
|---|---|---|
| Negative control | Not detected* | 0/1 |
| 21 CFU total | 36.60 | 5/5 |
| 21 CFU total | 36.17 | |
| 21 CFU total | 37.21 | |
| 21 CFU total | 38.81 | |
| 21 CFU total | 38.36 | |

*no fluorescence signal was detected after 50 amplification cycles.

EXAMPLE 6: DETECTION BY GROWING 117 CFU OF CANDIDA ALBICANS ON SOLID MEDIUM STARTING FROM 10 ML OF WHOLE BLOOD TREATED WITH 4% SAPONIN

In a 50-mL plastic tube, 10 mL of whole blood treated with EDTA was inoculated with 117 CFU of Candida albicans. The number of CFU inserted in the blood was verified by streaking on agar media in a Petri dish. Forty milliliters of filtered 4% saponin solution, 50 mM Tris-HCl at pH 8.0 and 4% of PEG-8000 were added to the inoculated blood. The tubes were agitated by inverting twice, incubated at room temperature for 5 minutes and centrifuged at 12000 g for 10 minutes. The pellets obtained were resuspended with 212 µl of Tryptone salt (AES) or 212 µl of mix of nucleases (Tris 10 mM pH7.5; DNAse I (Roche) 5000 u; RNAse If (New England Biolabs) 100 u), incubated for 10 minutes at room temperature and then streaked on a solid medium in a Petri dish SDC (bioMérieux). The number of colonies was then counted after incubating at 30° C. for 48 hours.

Table 6 shows that on average 66% of CFU were found after treatment with saponin with or without treatment with nucleases.

TABLE 6

Petri dish count of colonies of Candida albicans after treatment with 4% saponin

| Sample | Resuspension | Number of colonies | Mean value |
|---|---|---|---|
| 117 CFU total | Tryptone salt | 84 | 78.5 |
| 117 CFU total | Tryptone salt | 73 | (67% of 117) |
| 117 CFU total | Nuclease mix | 87 | 76 |
| 117 CFU total | Nuclease mix | 65 | (65% of 117) |

* no fluorescence signal was detected after 50 amplification cycles.

EXAMPLE 7: FACILITATING EFFECT OF PEG ON THE PRECIPITATION BY CENTRIFUGATION OF PSEUDOMONAS AERUGINOSA PRESENT IN BLOOD

200 µl of whole blood treated with EDTA was distributed in a 1.5-mL plastic tube. 1 mL of 10 mM $MgCl_2$ or 1 mL of $MgCl_2$ supplemented to final 4% of PEG was added to the tubes. Next, these tubes were inoculated with 129 CFU of Pseudomonas aeruginosa. The tubes were vortexed for 5 seconds and then centrifuged for 10 minutes at 5000 g. The pellets were then resuspended with 100 µl of Tryptone salt and then streaked on solid medium in a Petri dish TSA (bioMérieux). The dishes were incubated for 24 h at 37° C. prior to counting.

Addition of PEG contributed to a 23.5% improvement in precipitation yield (Table 7).

TABLE 7

Petri dish count of colonies of Pseudomonas aeruginosa
after centrifugation with or without the presence of PEG

| Sample | Precipitating solution | Number of colonies | Mean value |
|---|---|---|---|
| 129 CFU total | $MgCl_2$ | 66 | 70 |
| 129 CFU total | $MgCl_2$ | 74 | (54% of 129) |
| 129 CFU total | $MgCl_2$ + PEG | 100 | 100 |
| 129 CFU total | $MgCl_2$ + PEG | 100 | (77.5% of 129) |

\* no fluorescence signal was detected after 50 amplification cycles.

The invention claimed is:

1. A method for selective isolation of microorganisms of interest in a liquid biological sample comprising or likely to comprise:
  microorganisms of interest whose cell membrane or capsid does not contain cholesterol, and
  untargeted elements, i.e.:
    untargeted cells whose cell membrane contains cholesterol, and
    optionally, viruses with envelopes containing cholesterol, and
    optionally mycoplasmas containing cholesterol, and
    optionally, debris of microorganisms of interest and/or of untargeted cells,
  said method comprising the following steps:
    a) bringing the liquid biological sample into contact with a saponin formulation, in order to destabilize the cell membranes containing cholesterol or the viral envelopes containing cholesterol or the membranes of mycoplasmas containing cholesterol,
    b) performing osmotic shock of the untargeted cells in order to lyse them specifically,
    c) adding a solution of at least one enzyme able to lyse free nucleic acids derived from the untargeted elements lysed in solution in the sample, allowing the microorganisms of interest to be obtained selectively, and
    in step a), after steps a) and b), or after step c), adding an agent for precipitating the unlysed microorganisms of interest in solution in the sample.

2. The method according to claim 1, wherein the saponin formulation is present in a volume that is greater than or equal to a volume of the sample at the same concentration.

3. The method according to claim 1, wherein a concentration of saponin in the saponin formulation is greater than 0.02% and less than or equal to 20%.

4. The method according to claim 1, wherein the saponin formulation comprises a triterpenoid.

5. The method according to claim 1, wherein the enzyme able to lyse the free nucleic acids is then inactivated:
  chemically by adding ethylenediaminetetraacetic acid (EDTA), ethylene glycol tetraacetic acid (EGTA), dithiothreitol (DTT), β-mercaptoethanol, diethylpyrocarbonate (DEPC), and/or guanidine
  and/or
  physically by increasing a temperature of the sample to a temperature in a range of from 40 to 100° C.

6. The method according to claim 1, wherein the pH is maintained in a range of from 5 to 10 by adding a solution that is basic if the pH is below 5, and adding a solution that is acidic if the pH is above 10.

7. A method for selective isolation of microorganisms of interest in a liquid biological sample comprising or likely to comprise:
  microorganisms of interest whose cell membrane or capsid does not contain cholesterol, and
  untargeted elements, i.e.:
    untargeted cells whose cell membrane contains cholesterol, and
    optionally, viruses with envelopes containing cholesterol, and
    optionally mycoplasmas containing cholesterol, and
    optionally, debris of microorganisms of interest and/or of untargeted cells,
  said method comprising the following steps:
    a) bringing the liquid biological sample into contact with a saponin formulation, in order to destabilize the cell membranes containing cholesterol and/or the viral envelopes containing cholesterol and/or the membranes of the mycoplasmas containing cholesterol,
    b) performing osmotic shock of the untargeted cells in order to lyse them specifically,
    c) adding an agent for precipitating the unlysed microorganisms of interest in solution in the sample, allowing the microorganisms of interest to be obtained selectively.

8. The method according to claim 7, wherein the agent for precipitating the unlysed microorganisms of interest is selected from the group consisting of polyethylene glycol (PEG), glycogen, and nucleic acids.

9. The method according to claim 7, wherein a concentration of the agent for precipitating the unlysed microorganisms of interest is from 0.1 to 20%.

10. A method for selective isolation of nucleic acids of interest in a liquid biological sample, comprising or likely to comprise:
  microorganisms of interest whose cell membrane or capsid does not contain cholesterol, and
  untargeted elements, i.e.:
    untargeted cells whose cell membrane contains cholesterol, and
    optionally, viruses with envelopes containing cholesterol, and
    optionally mycoplasmas containing cholesterol, and
    optionally, debris of microorganisms of interest and/or of untargeted cells,
  said method comprising the following steps:
    a) bringing the liquid biological sample into contact with a saponin formulation, in order to destabilize the cell membranes containing cholesterol and/or the viral envelopes containing cholesterol and/or the membranes of mycoplasmas containing cholesterol,
    b) carrying out osmotic shock of the untargeted cells in order to lyse them specifically,
    c) adding a solution of at least one enzyme able to lyse free nucleic acids derived from the untargeted elements lysed in solution in the sample,
    d) inactivating the enzyme added in step (c),
    e) making accessible the nucleic acids of microorganisms of interest not degraded by the enzyme of step (c), and
    in step a), after steps a) and b), after step c), or after step d), adding an agent for precipitating the unlysed microorganisms of interest in solution in the sample.

11. A method for selective isolation of nucleic acids of interest in a liquid biological sample comprising or likely to comprise:
  microorganisms of interest whose cell membrane or capsid does not contain cholesterol, and untargeted elements, i.e.:
- untargeted cells whose cell membrane contains cholesterol, and
- optionally, viruses with envelopes containing cholesterol, and
- optionally mycoplasmas containing cholesterol, and
- optionally, debris of microorganisms of interest and/or of untargeted cells, said method comprising the following steps:
- a) bringing the liquid biological sample into contact with a saponin formulation, in order to destabilize the cell membranes containing cholesterol and/or the viral envelopes containing cholesterol and/or the membranes of the mycoplasmas containing cholesterol,
- b) carrying out osmotic shock of the untargeted cells in order to lyse them specifically,
- c) adding a precipitant of the unlysed microorganisms of interest in solution in the sample, and
- d) making accessible the nucleic acids of microorganisms of interest not accessible by the action of steps a) and b).

12. A method comprising contacting a liquid biological sample with a saponin formulation and a solution of at least one enzyme able to lyse free nucleic acids and at least one precipitant for isolation of microorganisms of interest or nucleic acids of microorganisms of interest, in the liquid biological sample.

13. The method according to claim 12, wherein:
a final concentration of the saponin formulation is greater than 0.02% and less than or equal to 20%,
a concentration of the precipitant is of from 0.1 to 20%, and/or
the enzyme able to lyse the free nucleic acids contains 500 to 20000 enzyme units.

14. The method according to claim 12, wherein a concentration of saponin in the saponin formulation is above 0.02% and less than or equal to 4%.

15. The method according to claim 12, the method having an analytical sensitivity greater than 1 CFU/mL.

16. The method according to claim 15, the method having an analytical sensitivity of at least 0.5 CFU/mL.

17. A diagnostic kit for isolating microorganisms of interest and/or nucleic acids of microorganisms of interest in a liquid biological sample, comprising or likely to comprise microorganisms of interest, untargeted cells and, optionally, enveloped viruses, mycoplasmas and/or debris of microorganisms of interest and/or of untargeted cells, said kit comprising:
- (a) a container,
- (b) at least one saponin formulation, and
- (c) at least one solution of a precipitant.

18. The kit according to claim 17, further comprising:
- (d) at least one enzyme able to lyse the nucleic acids.

19. The kit according to claim 17, further comprising one or more selected from the group consisting of:
- (d) at least one acid solution and/or at least one basic solution,
- (e) EDTA, EGTA, DTT, β-mercaptoethanol, DEPC, and/or guanidine, and
- (f) at least one detergent or an anionic agent.

* * * * *